United States Patent [19]
Lennon et al.

[11] Patent Number: 5,935,542
[45] Date of Patent: Aug. 10, 1999

[54] CYANPHOSPHONATE DERIVATIVES AND METHOD FOR THEIR PREPARATION

[75] Inventors: Patrick J. Lennon, Webster Grove; Sergey G. Vulfson, Chesterfiled, both of Mo.

[73] Assignee: Monsanto Company, St. Louis, Mo.

[21] Appl. No.: 08/997,339

[22] Filed: Dec. 23, 1997

Related U.S. Application Data

[60] Provisional application No. 60/034,513, Dec. 30, 1996.

[51] Int. Cl.⁶ ................... C07F 9/40; C07F 9/38; C07F 9/655
[52] U.S. Cl. ............ 423/302; 536/18.7; 558/167; 558/168; 564/281; 564/291; 564/292; 568/9; 568/18; 568/27
[58] Field of Search ............ 423/302; 564/281; 564/291, 292; 568/9, 18, 27; 558/167

[56] References Cited

U.S. PATENT DOCUMENTS

| | | |
|---|---|---|
| 2,402,703 | 6/1946 | Woodstock . |
| 2,702,299 | 2/1955 | Harris . |
| 3,432,277 | 3/1969 | Roesky .............................. 23/357 |
| 3,812,221 | 5/1974 | Braden et al. ..................... 260/968 |
| 4,221,583 | 9/1980 | Gaertner et al. . |
| 4,568,432 | 2/1986 | Rogers . |

FOREIGN PATENT DOCUMENTS

| | | | |
|---|---|---|---|
| 300 936 | 9/1992 | Germany ................. | C07F 9/40 |
| 96/15135 | 5/1996 | WIPO . | |

OTHER PUBLICATIONS

Abstract—Database WPI, Section Ch, Week 7615, Derwent Publications Ltd., London, GB; Class B04, AN 76-27192X, XP002061354 & JP 51 023 225 A (Nippon Chem. Ind. Co. Ltd.), Feb. 24, 1976.

Blanchard, J. "Préparation d–acides beta–amino–ethyl–phosphoniques" *Tetrahedron*; vol. 32, No. 4, 1976, Oxford GB, pp. 455–459, XP002061374.

Chemical Abstracts, vol. 093, No. 12, Sep. 22, 1980, Columbus, Ohio, US; abstract no. 123612, Zhurba, Y.I. et al. "Increase in the stability of silver complexes in the process of simultaneous developing and fixing" and ZH NAUCHN, PIRKL. FOTOGR. KINEMATOGR. (ZNPFAG, 00444561); 80; vol. 25(3); pp. 182–185, VSES. GOS; NAUCHNO–ISSLED. PROEKTN. INST. KHIM.–FOTOGR. PROM., Moscow USSR; XP002061352.

Dyatkina, N. et al. Synthesis and antiviral activity of some fluorinated nucleotide derivativers: NUCLEOSIDES NUCLEOTIDES (NUNUD5, 07328311); 94; col. 13 (1–3); pp. 325–337, ENGELHARDT INST. MOL. BIOL.; Mowcow; 117984, Russia XP002061348.

Kashemirov, B.A. "(E)–(Hydroxyimino)(hydroxymethoxyphosphinyl)acetic acid: Synthesis and pH dependent fragmentation," *Tetrahedron Letters*, vol. 36, No. 52, 1995, Oxford GB, pp. 9437–9440; XP002061351.

Albrecht et al., "Reaction of the Two–Component System Trialkyl Phosphite/Carbon Tetrachloride with Nucleophiles 3. Reaction in Presence of Trialkylammonium Salts," *Z. anorg. allg. Chem.* 552: 132–146 (1987) and English language translation.

Kashemirov et al., "Troika Acids: Synthesis, Structure, and Fragmentation Pathways of Novel α–(Hydroxyimino)phosphonacetic Acids," *J. Am. Chem. Soc.* 117: 7285–7286 (1995).

Shioiri et al., "Reaction of Diethyl Phosphorocyanidate(DEPC) with Carboxylic Acids. A New Synthesis of Carboxylic Esters and Amides," *Tetrahedron* 32(18): 2211–2217 (1976).

Tung et al., "A New Method for the Preparation of O,O'–Dialkylphosphoryl Cyanides," *Hua Hsueh Hsueh Pao* (*Acta Chimica Sinica*) 31(3): 199–202 (1965).

*Primary Examiner*—Michael G. Ambrose
*Attorney, Agent, or Firm*—Arnold, White & Durkee

[57] ABSTRACT

The novel cyanophosphonate compounds of the present invention include cyanophosphonate salts, cyanophosphonate monoacid salts, cyanophosphonate monoacid esters, cyanophosphonate monoester salts and cyanophosphonate methylester salts.

88 Claims, No Drawings

CYANPHOSPHONATE DERIVATIVES AND METHOD FOR THEIR PREPARATION

This application claims the benefit of provisional application Ser. No 60/034,513, filed Dec. 30, 1996.

BACKGROUND OF THE INVENTION

Organophosphorus compounds have numerous and varied applications, for example, in herbicides, insecticides, fertilizers, flame retardants and plasticizers and as precursors for the synthesis of other organophosphorus compounds. Cyanophosphonates and their derivatives are of particular interest due to their versatility in synthetic pathways and a wide range of chemistries can extend from both the phosphorus and cyano moieties.

McKenna et al., *J. Am. Chem. Soc.* 117:7285–86 (1995), describe the preparation of orthophosphoric acid, phosphorocyanidic acid and the dicyclohexylamine salt of phosphorocyanidic acid. The McKenna synthesis of phosphorocyanidic acid involved a multi-step pathway with acid catalyzed hydrolysis of Z-hydroxyiminophosphonic acid tetrasodium salt and had reportedly low yields. McKenna et al. also disclosed the preparation of phosphorocyanidic acid from dimethyl phosphorocyanidate by silyldealkylation with trimethylsilylbromide followed by quenching with methanol. The dicyclohexyl ammonium salt was also isolated from the acid by treatment with dicyclohexylamine. McKenna also reportedly prepared a half acid, half salt sodium methylcyanophosphonate by the reaction of sodium iodide and dimethylcyanophosphonate in acetone. McKenna also disclosed the preparation of orthophosphoric acid by acid hydrolysis of E-hydroxyiminophosphonic acid tetrasodium salt.

Shiori et al., *Tetrahedron* 32:2211 (1976), disclosed the preparation of dimethylcyanophosphonate from trimethylphosphite and cyanogen bromide. Diethylcyanophosphonate is commercially available from Aldrich Chemical Co. in 93% purity.

Tung et al., *Hua Hsueh Hsueh Pao (Acta Chimica Sinica)* 31(3):199–202 (1965), disclosed the preparation of O,O'-dialkyl phosphoryl cyanides by the reaction of sodium cyanide with dialkylphosphonates in the presence of carbon tetrachloride. Tung et al. reports that the method was used to prepare dimethylphosphoryl cyanide, diethylphosphoryl cyanide, di-n-propylphosphoryl cyanide and di-isobutylphosphoryl cyanide.

There exists a need for novel cyanophosphorus compounds and methods for their preparation to enable the preparation of organophosphorus materials with a variety of beneficial uses.

SUMMARY OF THE INVENTION

The novel cyanophosphonate compounds of the present invention include cyanophosphonate salts of the formula (I):

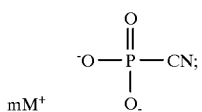

cyanophosphonate monoacid salts of the formula (II):

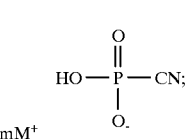

cyanophosphonate monoacid esters of the formula (III):

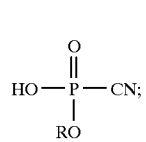

cyanophosphonate monoester salts of the formula (IV):

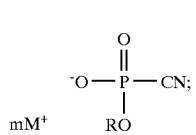

and cyanophosphonate methylester salts of the formula (V):

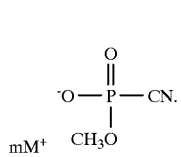

The compounds of formulas (I), (II), (III), (IV) and (V) can be prepared by a method that involves contacting trimethylsilyl iodide and diethylcyanophosphonate to form bis(trimethylsilyl)cyanophosphonate, and subsequently adding an alcohol to produce cyanophosphonic acid, which upon addition of a base produces the desired cyanophosphonate derivative. In a preferred embodiment, the cyanophosphonate salts can be subsequently hydrogenated to produce aminomethylphosphonate derivatives.

The methods and compositions according to the invention offer significant advantages in that they provide a novel, economic route to synthesize cyanophosphonate and aminomethylphosphonate derivatives having an improved environmental impact over conventional processes using halogen-containing phosphorus compounds.

DESCRIPTION OF ILLUSTRATIVE EMBODIMENTS

The novel cyanophosphonate compounds of the present invention include cyanophosphonate salts of the formula (I):

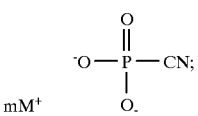

cyanophosphonate monoacid salts of the formula (II):

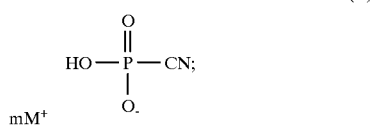

cyanophosphonate monoacid esters of the formula (III):

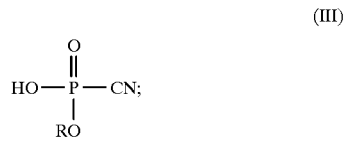

cyanophosphonate monoester salts of the formula (IV):

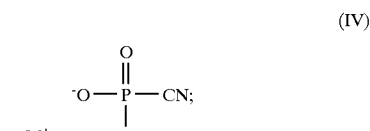

and cyanophosphonate methylester salts of the formula (V):

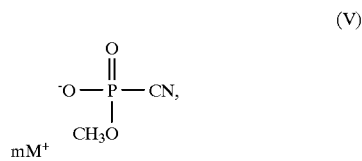

wherein $M^+$ is a suitable monovalent or polyvalent cation and m is a number, preferably an integer, indicating the number of $M^+$ cations for neutralization of the subject compound.

The compounds according to the invention can be prepared by a method that involves contacting trimethylsilyl iodide and diethylcyanophosphonate to form bis (trimethylsilyl)cyanophosphonate, and subsequently adding an alcohol to produce cyanophosphonic acid, which upon addition of base produces cyanophosphonate derivatives.

In one embodiment of this method, a reaction vessel is charged with diethylcyanophosphonate under nitrogen with cooling. Trimethylsilyl iodide is then added, preferably in an amount ranging from about 2 to 2.5 molar equivalents relative to diethylcyanophosphonate, and more preferably about 2.1 molar equivalents. The rate of trimethylsilyl iodide addition is adjusted so as to maintain the temperature of the reaction mixture below about 25° C. The reaction mixture is then allowed to warm to room temperature and excess trimethylsilyl iodide and generated ethyl iodide are removed under reduced pressure. The reaction mixture is then cooled and dry alcohol is added, preferably in an amount of about 2.5 to 3.5 molar equivalents relative to diethylcyanophosphonate, and more preferably about 3 molar equivalents.

A base is then added to the reaction mixture, which base can be an organic or inorganic base. When an organic base is used, the alcohol is first removed under reduced pressure, and replaced with methanol. The organic base is dissolved in methanol, and combined with the reaction mixture. The organic base is used preferably in an amount ranging from about 2 to 2.5 molar equivalents relative to diethylcyanophosphonate, and more preferably about 2.1 molar equivalents. Ether, and more preferably diethyl ether or tetrahydrofuran, can be added to precipitate the cyanophosphonate salt.

When an inorganic base is used, approximately half of the alcohol is first removed under reduced pressure. A solution of inorganic base in a minimal volume of water is added. The inorganic base is used preferably in an amount ranging from about 2 to 2.5 molar equivalents relative to diethylcyanophosphonate, and more preferably about 2.1 molar equivalents. Two discrete layers and a precipitate are formed. The bottom layer is separated from the top layer and precipitate. The bottom layer is dissolved in about 3 volumes of methanol and precipitated by addition of about 5 volumes of diethyl ether or acetone to produce a solid. The solid is combined with the precipitate and washed with cold dry acetone. The combined solids are dissolved in methanol containing about 10% (v/v) water and precipitated with dry diethyl ether. The solvent is removed under reduced pressure.

Diethylcyanophosphonate is commercially available, for example, from Aldrich Chemical Co. at assays of 93%.

The alcohol is generally any low boiling point alcohol suitable for participation in the reaction to form cyanophosphonic acid. In a preferred embodiment, the alcohol is 2-propanol, ethanol, or methanol. More preferably, the alcohol is 2-propanol.

The organic base is generally any organic base suitable for participating in the production of the inventive compounds. In a preferred embodiment, the organic base is isopropylamine, ethanolamine, trimethylamine, triethylamine, glycine ethyl ester, pyridine, N-methylmorpholine, N,N-dimethylaniline, dibenzylamine, diethylamine, tris[2-(2-methoxyethoxy)ethyl]amine, 4-dimethylamino pyridine, 4-tert-butylpyridine, 4-(5-nonyl) pyridine, 1,8-bis(dimethylamino)naphthalene, tertiary butylamine, phenanthroline, piperidene, pyrrolidine, pyrazole, aniline, a dendrimeric amine, sulfoxonium hydroxide, alkylsulfonium hydroxide, tetraalkylammonium hydroxide (such as tetramethylammonium hydroxide), a phosphazene base, phosphonium hydroxide, guanidinium hydroxide, paraquat hydroxide or diquat hydroxide. More preferably, the organic base is ethanolamine.

The inorganic base is generally any inorganic base suitable for participating in the production of the inventive compounds. In a preferred embodiment, the inorganic base is ammonia, hydrazine, sodium carbonate, potassium carbonate, potassium hydroxide, sodium hydroxide, lithium hydroxide, potassium methoxide, sodium methoxide, lithium methoxide, sodium hydride, potassium hydride, or lithium hydride. More preferably, the inorganic base is potassium hydroxide, sodium hydroxide or ammonia.

Alternatively, the compounds according to the invention can be prepared by one or more methods disclosed in co-pending U.S. application Ser. No. 08/996,945 entitled "Method for Preparing Cyanophosphonate Derivatives from Pyrophosphate or Polyphosphate Esters and Cyanide," by Patrick J. Lennon and Sergey G. Vulfson, filed Dec. 23, 1997; Ser. No. 08/996,949 entitled "Method for Preparing Cyanophosphonate Derivatives from Phosphoric Anhydride and Cyanide," by Patrick J. Lennon and Sergey G. Vulfson, filed Dec. 23, 1997; and Ser. No. 08/996,947 entitled "Method for Preparing Cyanophosphonate Derivatives from Phosphate Esters and Cyanide," by Patrick J. Lennon and Sergey G. Vulfson, filed Dec. 23, 1997.

The cyanophosphonate salts in formulas (I), (II), (IV) and (V) can be comprised of many different combinations of anions and cations. The cation(s) can generally be any monovalent or polyvalent cation compatable with the preparation of cyanophosphonate derivatives according to the inventive processes. Some general classes of cations suitable for the compounds of the invention include a hydrogen cation, an alkali metal cation, an alkaline earth metal cation, a transition metal cation, a group III metal cation, a lanthanide cation, an actinide cation, a cationic form of a primary amine, a cationic form of a secondary amine, a cationic form of a tertiary amine, a cationic form of a polyamine, a cationic form of an amino acid, a cationic form of a dendrimeric amine, a cationic form of a heterocycle, an ammonium cation, a quaternary ammonium cation, a cationic hydrazine derivative, an amidinium cation, a sulfoxonium cation, a sulfonium cation, a phosphonium cation, a phosphazenium cation, a guanidinium cation or a cationic form of a biologically active amine. These cations can include any suitable anionic component, provided that they possess an overall positive charge.

The alkali metal cation, for example, is preferably a lithium, sodium, or potassium cation. The alkaline earth metal cation is preferably a calcium or magnesium cation. The transition metal cation is preferably a cationic form of titanium, zirconium, chromium, manganese, iron, cobalt, nickel, ruthenium, osmium, rhodium, iridium, palladium, platinum, molybdenum, copper, silver, gold, zinc or cadmium. The group III metal cation is preferably a cationic form of aluminum, gallium or indium. The lanthanide cation is preferably a cationic form of lanthanum, cerium, praseodymium, neodymium, samarium, europium, gadolinium, terbium, dysprosium, holmium, erbium, thulium, ytterbium or lutetium. The actinide cation is preferably a cationic form of thorium or uranium.

The primary amine cation is preferably a cationic form of a straight chain alkyl amine, a branched chain alkyl amine, an aminoalcohol derivative, an arylamine, an arylalkylamine, a cycloalkyl amine, a polycycloalkyl amine or mixtures thereof. The straight chain alkyl amine cation is preferably a cationic form of methylamine, ethylamine, 1-propylamine, 1-butylamine, 1-pentylamine, 1-hexylamine, 1-heptylamine, 1-octylamine, 1-decylamine, 1-dodecylamine, 1-tetradecylamine or 1-hexadecylamine. The cationic form of branched chain alkyl amine is preferably a cationic form of 2-aminopropane, 2-aminobutane, 2-methyl-2-aminopropane, 2-methyl-1-aminopropane, 2-aminopentane, 3-aminopentane, 3-methyl-1-aminobutane, 2,2-dimethylaminopropane, 3-methyl-2-aminobutane, 1,1-dimethylaminopropane, 2-methyl-1-aminobutane, 1-methyl-1-aminobutane, 4-methyl-1-aminopentane, 3-methyl-1-aminopentane, 2-methyl-1-aminopentane, 1-methyl-1-aminopentane, 3,3-dimethyl-1-aminobutane, 2,3-dimethyl-1-aminobutane, 2,4-dimethyl-1-aminobutane, 1,2-dimethyl-1-aminobutane, 2,2-dimethyl-1-aminobutane, 1,1-dimethyl-1-aminobutane, 1,1,2-trimethylaminopropane, 3-methyl-3-aminopentane, 2-ethyl-1-aminobutane, 2-heptylamine or 2-octylamine.

The cationic form of aminoalcohol derivative is preferably a cationic form of 2-ethanolamine, 2-methoxyethylamine, 3-methoxy-1-propylamine, 2-(2-aminoethoxy)-ethanol, 3-amino-1-propanol or 3-ethoxypropylamine. The cationic form of arylamine is preferably a cationic form of aniline, o-toluidine, m-toluidine, p-toluidine, 2,3-xylidine, 2,4-xylidine, 2,5-xylidine, 2,6-xylidine, 3,4-xylidine, 3,5-xylidine, o-aminophenol, m-aminophenol, p-aminophenol, o-nitroaniline, m-nitroaniline, p-nitroaniline, benzidine, o-tolidine, o-phenylenediamine, m-phenylenediamine or p-phenylenediamine. The cationic form of arylalkylamine is preferably a cationic form of benzylamine or β-phenylethylamine. The cationic form of cycloalkylamine is preferably a cationic form of cyclobutylamine, cyclopentylamine, cyclohexylamine, cycloheptylamine or cyclo-octylamine. The cationic form of polycycloalkylamine is preferably a cationic form of: 1-aminodecalin, 2-aminodecalin, 1-aminotetralin, 2-aminotetralin, 1-adamantamine or 2-adamantanamine.

The cationic form of secondary amine is preferably a cationic form of dimethylamine, diethylamine, dipropylamine, diisopropylamine, dibutylamine, dihexylamine, diphenylamine, diethanolamine, dibenzylamine, methylethylamine, di(2-methoxyethyl)amine, ditridecylamine, N-methylaniline, N-ethylaniline, N-methylcyclohexylamine, N-methylethanolamine or N-ethylcyclohexylamine. The cationic form of tertiary amine is preferably a cationic form of trimethylamine, triethylamine, tripropylamine, tributylamine, tripentylamine, triisopropylamine, N,N-dimethylbutyl amine, N,N-dimethylethyl amine, N,N-dimethylcyclohexylamine, N-methylcyclohexylamine, diisopropylethylamine, tris[2-(2-methoxyethoxy)ethyl]amine, N-dimethylaniline, 1,8-bis(dimethylamino)naphthalene, tribenzylamine, triphenylamine, N,N-dimethylethanolamine, N,N-dimethylaminodiglycol or N,N-diethylethanolamine. The cationic form of polyamine is preferably a cationic form of histamine, dopamine, isophorone diamine, polylysine, polyhistidine, 1,2-diaminocyclohexane, ethylenediamine, diethylenetriamine, triethylenetetramine, tetraethylenepentamine, polyallylamine, tetramethylethylene diamine, polyvinylpyridine, pentaethylenehexamine, N,N-bis(3-aminopropyl)methylamine, 2-(diethylamino)ethylamine, 3-(diethylamino)propylamine, 3,3'-dimethyl-4,4'-diaminodicyclohexylmethane, 3-(dimethylamino)propylamine, iminobispropylamine, 3-(methylamino)propylamine, neopentanediamine, N,N,N,N,N-pentamethyldiethylenetriamine, 1,2-propylenediamine, N,N,N',N'-tetramethyl-1,6-hexanediamine, N-(2-aminoethyl)ethanolamine, 1,6-diaminohexane-N,N,N',N'-tetraacetic acid or 4,7,10-trioxatridecane-1,13-diamine.

The cationic form of amino acid is preferably a cationic form of a natural amino acid, an unnatural amino acid, an ester of an amino acid or an amide of an amino acid. The cationic form of natural amino acid is preferably a cationic form of L-alanine, L-cysteine, L-aspartic acid, L-glutamic acid, L-phenylalanine, glycine, L-histidine, L-isoleucine, L-lysine, L-leucine, L-methionine, L-asparagine, L-proline, L-glutamine, L-arginine, L-serine, L-threonine, L-valine, L-tryptophan, L-tyrosine, selenocysteine, β-alanine, isoglutamine, norleucine, norvaline, ornithine, penicillamine, pyroglutamic acid, sarcosine, statine, homoserine, p-aminobenzoic acid or γ-aminobutyric acid. The cationic form of unnatural amino acid is preferably a cationic form of D-alanine, D-cysteine, D-aspartic acid, D-glutamic acid, D-phenylalanine, D-histidine, D-isoleucine, D-lysine, D-leucine, D-methionine, D-asparagine, D-proline, D-glutamine, D-arginine, D-serine, D-threonine, D-valine, D-tryptophan, D-tyrosine, hydroxyethyl-cysteine, trans-3-methylproline, iminodiacetic acid, homoglutamine, nitroglutamine, allo-threonine, hydroxyethylhomocysteine, α, α, α-trifluoroalanine or pipecolic acid.

The cationic form of ester of an amino acid is preferably a cationic form of an alkyl ester or an aryl ester. The cationic form of alkyl ester of an amino acid is preferably a cationic form of alanine methyl ester, cysteine methyl ester, aspartic acid methyl ester, glutamic acid methyl ester, phenylalanine methyl ester, glycine methyl ester, histidine methyl ester, isoleucine methyl ester, lysine methyl ester, leucine methyl ester, methionine methyl ester, asparagine methyl ester, proline methyl ester, glutamine methyl ester, arginine methyl ester, serine methyl ester, threonine methyl ester, valine methyl ester, tryptophan methyl ester, tyrosine methyl ester, sarcosine methyl ester, iminodiacetic acid dimethyl ester, alanine ethyl ester, cysteine ethyl ester, aspartic acid ethyl ester, glutamic acid ethyl ester, phenylalanine ethyl ester, histidine ethyl ester, isoleucine ethyl ester, lysine ethyl ester, leucine ethyl ester, methionine ethyl ester, asparagine ethyl ester, proline ethyl ester, glutamine ethyl ester, arginine ethyl ester, serine ethyl ester, threonine ethyl ester, valine ethyl ester, tryptophan ethyl ester, tyrosine ethyl ester, iminodiacetic acid diethyl ester, sarcosine ethyl ester, aspartic dimethyl ester, aspartic diethyl ester, glutamic dimethyl ester or glutamic diethyl ester.

The cationic form of aryl ester of an amino acid is preferably a cationic form of alanine benzyl ester, cysteine benzyl ester, aspartic acid benzyl ester, aspartic acid dibenzyl ester, glutamic acid benzyl ester, glutamic acid dibenzyl ester, phenylalanine benzyl ester, glycine benzyl ester, histidine benzyl ester, isoleucine benzyl ester, lysine benzyl ester, leucine benzyl ester, methionine benzyl ester, asparagine benzyl ester, proline benzyl ester, glutamine benzyl ester, arginine benzyl ester, serine benzyl ester, threonine benzyl ester, valine benzyl ester, tryptophan benzyl ester, tyrosine benzyl ester or sarcosine benzyl ester. The cationic form of an amide of an amino acid is preferably a cationic form of alaninamide, cysteinamide, aspartic acid amide, aspartic acid diamide, glutamic acid amide, glutamic acid diamide, phenylalaninamide, glycinamide, histidinamide, isoleucinamide, lysinamide, leucinamide, methioninamide, asparaginamide, prolinamide, glutaminamide, argininamide, serinamide, threoninamide, valinamide, tryptophanamide, tyrosinamide, sarcosinamide or γ-aminobutyric acid amide. The cationic form of dendrimeric amine is preferably a cationic form of poly(propyleneimine) or poly-(amidoamine). The cationic form of a heterocycle is preferably a cationic form of cis-2,6-dimethylmorpholine, N,N'-dimethylpiperazine, 2,2'-dimorpholinodiethylether, N-ethylpiperidine, N-methylpiperidine, morpholine, N-methyl-morpholine, 1,3,5-tris(dimethylaminopropyl)-sym-hexahydrotriazine, phenanthroline, pyrrolidine, piperidine, piperazine, quinuclidine, pyridine, 4-t-butylpyridine, 4-dimethylaminopyridine, 4-(5-nonyl) pyridine, pyrrole, oxazole, indole, isoxazole, purine, 1-azabicyclo[2.2.1]heptane, carbazole, imidazole, thiazole, pyrazole, isothiazole, quinoline, isoquinoline, quinoxaline, pyridazine, pyrimidine, pyrazine, methylpyridine, dimethylpyridine, 2,4,6-trimethyl-pyridine, nicotinamide, nicotinic acid methyl ester, nicotinic acid ethyl ester, nicotinic acid benzyl ester or 2-chloro-4-ethylamino-6-isopropylamino-1,3,5-triazine (atrazine).

The ammonium cation is preferably a cationic form of ammonium, tetramethyl ammonium, tetraethyl ammonium, tetrapropyl ammonium, tetrabutyl ammonium, tetraphenyl ammonium, paraquat, diquat, hexadecyltrimethyl ammonium, dodecyltrimethyl ammonium, octyltrimethyl ammonium, benzyldimethylhexadecyl ammonium, benzyldimethyldodecyl ammonium, benzyldimethyloctyl ammonium, cetyltrimethyl ammonium, 1-methylpyridinium, 1-ethylpyridinium, 1-hexadecylpyridinium, 1-dodecylpyridinium, 1-(1-adamantyl)pyridinium or 1-(carboxymethyl)pyridinium.

The cationic form of ammonium can also be a methyl, ethyl, propyl or butyl ester of triethylammonium, tripropylammonium, tributylammonium, tripentylammonium, trihexylammonium, triheptylammonium or trioctylammonium. The hydrazine derivative cation is preferably a cationic form of hydrazine, 2,4-dinitrophenylhydrazine, hydrazinobenzoic acid, 1,1-dimethylhydrazine, 1,1-diphenylhydrazine or 1,2-diphenylhydrazine. The amidinium cation is preferably a cationic form of creatine. The sulfoxonium cation is preferably a cationic form of trimethylsulfoxonium.

The sulfonium cation is preferably a cationic form of trimethylsulfonium, diphenyl methylsulfonium, triphenylsulfonium, triethylsulfonium, diphenyl ethylsulfonium or dimethylphenacylsulfonium. The phosphonium cation is preferably a cationic form of tetramethylphosphonium, tetraethylphosphonium, tetrabutylphosphonium, tetraphenyl phosphonium or tetrakis(hydroxymethol)phosphonium. The cation can be a guanidinium cation or a phosthazenium cation. The cationic form of biologically active amine is preferably a cationic form of chlorhexidine, mafenide, hexamethylpararosaniline, aminacrine, ethoxazene, phenazopyridine, amikacin, gentamicin, kanamycin, bekanamycin, neomycin, streptomycin, tobramycin, lincomycin, clindamycin, erythromycin, colistin, polymyxin B, tetracycline, chlorotetracycline, rolitetracycline, oxytetracycline, spectino-mycin, viomycin, bacampicyline, stallimycin, tromantadine, miconazole, econazole, chlormiconazole, chlormidazole, isoconazole, bifonazole, diamthazole, halethazole, hexetidine, phosphazene, indole or indoleacetic acid.

In a preferred embodiment, the cation is herbicidally active or compatible with the herbicidal activity of an anion with which it is associated. The cation is also preferably environmentally acceptable.

The particular cations to be used in the formula (I), (II), (IV) and (V) cyanophosphonate salts may vary. Compounds of the formula (I) preferably have a cation of an alkali metal cation, an alkaline earth metal cation, a transition metal cation, a group III metal cation, a lanthanide cation, an actinide cation, a cationic form of a primary amine, a cationic form of a secondary amine of molecular weight less than 175 g/mol, a cationic form of a secondary amine of molecular weight greater than 185 g/mol, a cationic form of a tertiary amine, a cationic form of a polyamine, a cationic form of an amino acid, a cationic form of a dendrimeric amine, a cationic form of a heterocycle, an ammonium cation, a quarternary ammonium cation, a cationic hydrazine derivative, an amidinium cation, a sulfoxonium cation, a sulfonium cation, a phosphonium cation, a guanidinium cation, a cationic form of a biologically active amine or mixtures thereof. The members of these cationic classes are the same as defined above, except that the secondary amine is preferably of a molecular weight below 175 g/mol, more preferably below 100 g/mol, and most preferably below 60 g/mol. The secondary amine is further preferably dimethylamine, diethylamine, dipropylamine, diisopropylamine, dibutylamine, dihexylamine, diphenylamine, diethanolamine, dibenzylamine, methylethylamine, di(2-methoxyethyl)amine, ditridecylamine, N-methylaniline, N-ethylaniline, N-methylcyclohexylamine, N-methylethanolamine, N-ethylcyclohexyl amine, diallylamine or dipropargylamine, and more preferably, dimethylamine.

In a preferred embodiment, the cyanophosphonate salt of formula (I) is a dipotassium, disodium or dilithium cyanosphosphonate. The cyanophosphonate salts of formula (I) can also be comprised of two different monovalent cations, preferably combinations of cationic forms of potassium and sodium, lithium and sodium, potassium and lithium, ammonium and sodium, ammonium and potassium, ammonium and a sulfonium, a sulfonium and alkylammonium, ammonium and alkylammonium, sodium and a sulfonium, potassium and a sulfonium, sodium and alkylammonium or potassium and alkylammonium.

The cyanophosphonate salts of formula (I) may alternatively comprise two identical monovalent cations and one cyanophosphonate anion, one divalent cation and one cyanophosphonate anion, two identical trivalent cations and three cyanophosphonate anions, two different trivalent cations and three cyanophosphonate anions. Alternatively, the cyanophosphonate salt can be a non-stoichiometric salt.

The cyanophosphonate monoacid derivative of formula (II) can be comprised of one monovalent cation and one cyanophosphonate monoacid anion, one divalent cation and two cyanophosphonate monoacid anions, one trivalent cation and three cyanophosphonate monoacid anions or a non-stoichiometric salt. The counterion for the monoacid monosalt cyanophosphonate derivatives can be any of the cations described for cyanophosphonate salts, and additionally, the cationic form of dicyclohexylamine.

In a preferred embodiment, the cyanophosphonate monoacid salt of formula (II) is potassium, sodium or lithium cyanophosphonate.

The formula (III) cyanophosphonate acid esters compounds have an R group, which can be defined as an alkyl, aryl, arylalkyl or functionalized group containing 2 to 20 carbons.

The alkyl group is preferably ethyl, allyl, propargyl, 1-propyl, 2-propyl, 1-butyl, 2-butyl, 2-methyl-2-propyl, 2-methyl-1-propyl, 1-pentyl, 2-pentyl, 3-methyl-1-butyl, 2,2-dimethyl-1-propyl, 1,2-dimethyl-1-propyl, 1,1-dimethyl-1-propyl, 2-methyl-1-butyl, 2-methyl-2-butyl, 3-pentyl, 1-hexyl, 2-hexyl, 3-hexyl, 4-methyl-1-pentyl, 3-methyl-1- pentyl, 2-methyl-1-pentyl, 1-methyl-1-pentyl, 3,3-dimethyl-1-butyl, 2,3-dimethyl-1-butyl, 2,4-dimethyl-1-butyl, 2,3-dimethyl-1-butyl, 2,2-dimethyl-1-butyl, 1,1-dimethyl-1-butyl, 1,1,2-trimethyl-1-propyl, 3-methyl-3-pentyl, 2-ethyl-1-butyl, 1-heptyl, 2-heptyl, 1-octyl 2-octyl, 1-decyl, 2-decyl, 1-dodecyl, 2-dodecyl, 1-tetradecyl, 2-tetradecyl, 1-hexadecyl, 2-hexadecyl, 1-octadecyl, 2-octadecyl, 1-eicosyl or 2-eicosyl. The aryl group is preferably phenyl. The arylalkyl group is preferably benzyl or β-phenylethyl. The functionalized group is preferably protonated 2-aminoethyl, choline, 2-hydroxyethyl, glycerol, propylene glycol, serine, threonine, tyrosine, glucose, sucrose, fructose, galactose, mannose, pentaerythritol, tetra (hydroxymethyl)methane or tetrakis (hydroxymethyl) phosphonium.

The formula (IV) compounds also have an R group, which is defined as any of the functionalities previously listed for the cyanophosphonic acid ester derivative class, and additionally, 2-aminoethyl. The cyanophosphonate monoester salts of formula (IV) also have a cationic component and can be comprised of one monovalent cation and one cyanophosphonate monoester anion, one divalent cation and two cyanophosphonate monoester anions, one trivalent cation and three cyanophosphonate monoester anions, or the cyanophosphonate monoester salt can be a non-stoichiometric salt. The cation can be any of those listed above.

The formula (V) cyanophosphonate methylester salts have a cationic component defined as any of those applicable for the general class of cyanophosphonate monoester salt derivatives, except sodium. The cyanophosphonate monomethylester salt can comprise a monovalent cation and one cyanophosphonate monomethylester anion, one divalent cation and two cyanophosphonate monomethylester anions, one trivalent cation and three cyanophosphonate monomethylester anions or the cyanophosphonate monomethylester salt can be a non-stoichiometric salt.

The novel compounds according to the invention include disodium cyanophosphonate, dipotassium cyanophosphonate, bis(2-hydroxyethylammonium) cyanophosphonate, bis(ammonium)cyanophosphonate, bis (isopropylammonium)cyanophosphonate, bis (dimethylammonium)cyanophosphonate, mono (isopropylammonium)-cyanophosphonate, bis (trimethylsulfonium)cyanophosphonate, isopropylammonium ethyl cyanophosphonate, (ethyl 2-ammonium acetate)ethyl cyanophosphonate, trimethylsulfonium ethyl cyanophosphonate, tetramethylphosphonium ethyl cyanophosphonate and sodium ethyl cyanophosphonate.

The cyanophosphonate derivatives of the invention can be used as precursors for producing other organophosphorus species. In a preferred embodiment, the cyanophosphonate derivative is hydrogenated to produce an aminomethylphosphonate derivative. The hydrogenation can take place by contacting the cyanophosphonate derivative with hydrogen in the presence of a suitable catalyst under sufficient conditions to produce an aminomethylphosphonate derivative. The cyanophosphonate derivative may be provided alone or in a mixture of compounds, including product mixtures or portions of product mixtures from a cyanophosphonate derivative-producing reaction.

Preferably, the hydrogenation further involves the presence of a solvent. The solvent can be any material that enhances the solubility of reactants or promotes the formation of the desired products. In a preferred embodiment, the solvent is water, acetic acid, an alcohol, dimethylacetamide, an anhydride, e.g., acetic anhydride, an amide, sulfolane or mixtures thereof.

Hydrogen pressure can be maintained at a level suitable for the formation of an aminomethylphosphonate derivative, and consistent with safety limitations of the experimental system. In a preferred embodiment, the hydrogen pressure is between about 0.25 and 5000 psi, more preferably between about 0.5 and about 3000 psi and most preferably between about 1 and about 1000 psi, for example, between about 25 and about 300 psi.

In a preferred embodiment, the catalyst is a transition metal catalyst. For example, the hydrogenation step can use a catalyst of a cobalt-containing compound, a nickel-containing compound, a platinum-containing compound, a palladium-containing compound or a rhodium-containing compound. More preferably, the catalyst is Raney cobalt, Raney nickel, a platinum promoted Raney nickel such as platinum tetrachloride ($PtCl_4$) promoted Raney nickel, platinum on carbon, palladium on carbon or rhodium on carbon. The catalyst can be used at a stoichiometric amount or catalytic amount with respect to the cyanophosphonate derivative. The stoichiometric amount is preferably between about 1 molar equivalent and 5 molar equivalents with respect to the cyanophosphonate derivative, and more preferably between about 1 molar equivalent and 2 molar equivalents with respect to the cyanophosphonate derivative. The catalytic amount is preferably between about 0.1 molar percent and 100 molar percent with respect to the cyanophosphonate derivative, and more preferably between about 0.5 molar percent and 50 molar percent with respect to the cyanophosphonate derivative.

In the event that a catalyst of platinum on carbon, palladium on carbon or rhodium on carbon is used, the hydrogenation reaction mixture preferably further contains an acid in an amount sufficient to promote formation of the desired product. The acid can be an inorganic acid or an organic acid. The inorganic acid is preferably hydrochloric acid, sulfuric acid, phosphoric acid, nitric acid or hydrocyanic acid and, more preferably, hydrochloric acid. The organic acid is preferably acetic acid, trifluoroacetic acid, trifluoromethanesulfonic acid, or p-toluenesulfonic acid. The acid can be present at a concentration between about 0.1 and 5 molar equivalents with respect to the cyanophosphonate derivative, more preferably at a concentration between about 0.5 and 2.5 molar equivalents with respect to the cyanophosphonate derivative, and most preferably at a concentration of about 1 molar equivalent or about 2 molar equivalents with respect to the cyanophosphonate derivative, depending on the degree of protonation.

In a preferred embodiment the reaction product mixture from the hydrogenation step is heated under sufficient conditions to further promote the formation of the aminomethylphosphonate derivative. For example, a product mixture that has been partially or substantially hydrogenated can be heated to a temperature in the range of about 135° C. to about 200° C., and more preferably to a range of about 135° C. to about 160° C. This heating step may be conducted for any amount of time that further promotes the aminomethylphosphonate derivative formation, preferably about 1 to about 12 hours. The heating time for optimum aminomethylphosphonate derivative formation can depend on the pH and the nature of the cations in the reaction mixture.

The products of the hydrogenation step can be isolated from the reaction mixture by conventional methods or can be used for some purposes without isolation from the reaction product mixture. Further details regarding cyanophosphonate derivative hydrogenation are provided in co-pending U.S. application Ser. No. 08/996,948 entitled "Method for Preparing Aminomethylphosphonate Derivatives Via Hydrogenation of Cyanophosphonate Derivatives," by Patrick J. Lennon, filed Dec. 23, 1997, which is incorporated herein by reference.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

General Procedure for Examples 1 to 11

Trimethylsilyl iodide (2.1 to 2.7 equivalents) was added to one equivalent of diethyl cyanophosphonate cooled in ice-water bath and magnetically stirred. The ice bath was removed and the temperature of the reaction mixture was allowed to rise to room temperature during 3 to 10 minutes. The volatile components were removed under vacuum. Dry isopropanol (three equivalents) was added to the residue cooled in an ice or dry ice-acetone bath. For deprotonation using an organic base, the isopropanol was evaporated and replaced by methanol, acetone or $CH_2Cl_2$ (0.5 ml per mmol $(HO)_2POCN$), and cooled using a dry ice-acetone bath. The base (2.0 to 2.2 equivalents) was added as a solution in methanol or THF (0.5 ml per mmol $(HO)_2POCN$). Addition of ether or THF precipitated the salt. Inorganic bases (2 to 2.2 equivalents) were added in a minimal volume of water to the isopropanol solution of $(HO)_2P(O)CN$. As a result, two layers and a precipitate were formed. The bottom layer and the precipitate were separated from the top (isopropanol) layer. The precipitate was filtered. The bottom layer was dissolved in three volumes of methanol, and precipitation of product was effected by addition of about five volumes of ethyl ether or acetone to give a white solid. This product was combined with the first precipitate and washed with cold, dry acetone. Reprecipitation from 10% aqueous methanol (1 g salt in 30 ml solution) by addition of dry ethyl ether gave the product, which was dried overnight under vacuum.

Example 1

Disodium Cyanophosphonate

This reaction was carried out with diethyl cyanophosphonate (15 g, 0.092 mol) and trimethylsilyl iodide (50 g, 0.25 mol). After removing the volatile components under vacuum, isopropyl alcohol (15 ml) was added at 0° C. and then 8 ml of aqueous solution containing NaOH (3.7 g, 0.09 mol) was added. A white precipitate was formed which was filtered, and dissolved in a 10:1 methanol-water solution (110 mL). Ethyl ether (500 mL) was added, precipitating a white solid, which was filtered and dried, yielding 11.8 g of product (85% yield). $^{31}P$ NMR ($D_2O$) δ (ppm) −17.0; $^{13}C$ NMR ($D_2O$) δ (ppm) 123.4 (d, $^1J_{CP}$=143.7 Hz). Elemental analysis. Found: C, 7.65%; H, <0.5%; N, 8.76%; $H_2O$, 2.99% (Karl Fisher titration). Calculated for $Na_2O_3PCN$ $(H_2O)_{0.26}$: C, 7.72%; H, 0.34%; N, 9.00%.

Example 2

Dipotassium Cyanophosphonate

The reaction was carried out with diethyl cyanophosphonate (9.0 g, 0.055 mol) and trimethylsilyl iodide (25 g, 0.125 mol). After removing the volatile components under vacuum, the residue was cooled to −30° C. and isopropyl alcohol (12 ml) was added, followed by aqueous KOH (10 mL containing 6.15 g, 0.11 mol of KOH). A white precipitate formed, which was filtered and washed with acetone (30 mL), yielding 9.1 g of crude product (91% yield) after drying under vacuum. This material was quite pure, containing about 2.2% of inorganic phosphate. It could be further purified by dissolution in a mixture of methanol (60 mL) and water (6 mL), and precipitation by addition of ethyl ether (500 mL), giving 5.6 g (53%) of pure salt. $^{31}P$ NMR ($D_2O$) δ (ppm) −16.8; $^{13}C$ NMR ($D_2O$) δ (ppm) 123.3 (d, $^1J_{CP}$=142.8 Hz). Elemental analysis: Found, C, 6.69%; H, 0.40%; N, 7.21%; $H_2O$, 2.19% (Karl Fisher titration). Calculated for $(KO)_2POCN(H_2O)_{0.23}$, C, 6.41%; H, 0.25%; N, 7.48%.

Example 3

Bis(2-hydroxyethylammonium)Cyanophosphonate

This reaction was carried out with diethyl cyanophosphonate (2.0 g, 12.26 mmol) and trimethylsilyl iodide (5.35 g, 26.74 mmol). After removing the volatile components under reduced pressure, isopropanol (3 mL) was added at 0° C., forming cyanophosphonic acid which was not isolated. The isopropanol was evaporated and replaced with acetone (6 mL) and the solution was cooled to −25° C. 2-Aminoethanol (1.7 g, 28.86 mmol) in methanol (4 mL) was added, causing a white precipitate to form. It was filtered, yielding 2.38 g of crude product (84% yield) which was dissolved in methanol (10 mL) and precipitated by addition of excess ether, yielding 1.6 g (6.93 mmol, 57%) of pure salt. $^{31}$P NMR (D$_2$O) δ (ppm) −14.5; $^{13}$C NMR (D$_2$O) δ (ppm) 124.5 (d, $^1J_{CP}$=145.7 Hz). Mass spectrum: (FAB$^+$ DTT:DTE, 1:1) m/z 230, corresponds to the protonated form of the salt [(H$_3$N(CH$_2$)$_2$OH)$_2$O$_2$POCN+H$^+$], the cation (H$_3$N(CH$_2$)$_2$OH)$^+$ at m/z 62; Negative ion (FAB$^-$ DTT:DTE, 1:1) m/z 106 [(NC)P(O)(OH)O$^-$]. High resolution mass spectroscopy: Observed mass, 230.0901. Calculated mass for [C$_5$H$_{16}$PN$_3$O$_5$+H]$^+$, 230.0906. Elemental analysis: Found, C, 26.03%; H, 6.92%; N, 17.87%; H$_2$O, 0.74% (Karl Fisher titration). Calculated for (H$_3$N(CH$_2$)$_2$OH)$_2$O$_2$POCN(H$_2$O)$_{0.1}$, C, 26.02%; H, 7.07%; N, 18.21%.

Example 4
Bis(ammonium)Cyanophosphonate

Cyanophosphonic acid was prepared as in Example 3 using the same molar quantities. After isopropanol was added, it was removed under reduced pressure and 3.35 g of 28.4% aqueous solution of NH$_4$OH (27.11 mmol base) was slowly added at −20° C. A white precipitate was formed. It was diluted with dry, cold methanol (5 mL) and filtered giving 1.5 g of salt (10.6 mmol, 86% yield). $^{31}$P NMR (D$_2$O) δ (ppm) −15.1; $^{13}$C NMR (D$_2$O) δ (ppm) 123.1 (d, $^1J_{CP}$= 146.3 Hz). Elemental analysis: Found, C, 8.74%; H, 5.72%; N, 29.55%; H$_2$O, 0.32% (Karl Fisher titration). Calculated for (H$_4$N)$_2$O$_2$PO—CN(H$_2$O)$_{0.03}$, C, 8.48%; H, 5.74%; N, 29.67%.

Example 5
Bis(isopropylammonium)Cyanophosphonate

Cyanophosphonic acid was prepared with isopropanol according to the procedure in Example 3 using the same molar quantities. The isopropanol was removed under reduced pressure and replaced with methanol (6 mL). To this solution isopropyl amine (1.7 g, 0.029 mol) in methanol (2 mL) was slowly added at −20° C. A white precipitate formed. It was filtered and dried (2.16 g), then dissolved in a 10:1 mixture of methanol and ether (20 mL) and precipitated by addition of ether (50 mL), yielding 1.8 g of the product (7.97 mmol, 65% yield). $^{31}$P NMR (D$_2$O) δ (ppm) −15.5; $^{13}$C NMR (D$_2$O) δ (ppm) 123.4 (d, $^1J_{CP}$=144.3 Hz). Mass spectrum (FAB$^+$ DTT:DTE, 1:1) m/z 226, corresponding to the protonated form of the salt [(NH$_3$CH(CH$_3$)$_2$)$_2$O$_2$POCN+H$^+$], m/z 60 ([NH$_3$CH(CH$_3$)$_2$]$^+$); Negative ion: (FAB$^-$ DTT:DTE, 1:1) m/z 106 [NCP(O)(OH)O$^-$]. High resolution mass spectroscopy: Observed mass, 226.1323. Calculated mass for [C$_7$H$_{20}$PN$_3$O$_3$+H]$^+$, 226.1320. Elemental analysis. Found: C, 37.06%; H, 8.85%; N, 18.45%; H$_2$O, 0.28% (Karl Fisher titration). Calculated for (NH$_3$CH(CH$_3$)$_2$)$_2$—O$_2$POCN(H$_2$O)$_{0.03}$: C, 37.24%; H, 8.96%; N, 18.61%.

Example 6
Bis(dimethylammonium)Cyanophosphonate

Cyanophosphonic acid was prepared using isopropanol according to the procedure described in Example 3. The isopropanol was removed under reduced pressure and replaced by dry acetone (10 mL). To this solution 20 mL of a 2M solution of NH(CH$_3$)$_2$ (40 mmol) in THF were slowly added at −20° C. A white precipitate formed which was filtered and washed three times with dry, cold acetone (50 mL each). After drying under vacuum, 2.3 g of crude product were obtained. They were filtered and washed 3 times with 50 mL of dry and cold acetone and once with 10 mL of ether, and dried under vacuum overnight, giving the product as a white solid (1.7 g, 8.60 mmol, 70% yield). $^{31}$P NMR (D$_2$O) δ (ppm)−15.4; $^{13}$C NMR (D$_2$O) δ (ppm) 124.1 (d, $^1J_{CP}$= 145.2 Hz). Mass spectrum (FAB$^+$ DTT:DTE, 1:1) m/z 198, corresponding to the protonated form of salt [(NH(CH$_3$)$_2$)$_2$O$_2$POCN+H$^+$], m/z 46 [(NH(CH$_3$)$_2$)$^+$]; Negative ion (FAB$^-$, DTT:DTE, 1:1) at m/z 106 [NCP(O)(OH)O$^-$]). High resolution mass spectroscopy: Observed mass, 198.1002. Calculated mass for [C$_5$H$_{16}$PN$_3$O$_3$+H$^+$], 198.1007.

Example 7
Mono(isopropylammonium)Cyanophosphonate

Cyanophosphonic acid was prepared according to the procedure described in Example 3 using the same molar quantities. The isopropanol was removed and replaced by 6 mL of a mixture of dry acetone and ether (2:1). To this solution, isopropyl amine (0.72 g, 12.18 mmol) dissolved in 6 mL of a mixture of dry acetone and ether (2:1) was slowly added at −30° C. A clear solution was formed. Solvent was removed to give a yellow oil, which was dissolved in 10 mL of dry methanol. To this solution 20 mL of a solution of ether and acetone (5:1) was added. A small amount (about 0.1 g) of white crystals precipitated. They were removed from the solution which was then evaporated to give a solid residue. The solid was washed twice with 10 mL of chloroform, yielding 0.6 g (3.61 mmol) of the monosalt (30% yield). $^{31}$P NMR (D$_2$O) δ (ppm) −21.1; $^{13}$C NMR (D$_2$O) δ (ppm) 119.2 (d, $^1J_{CP}$=176.9 Hz); Mass spectrum (FAB$^+$ DTT:DTE, 1:1) m/z 167, corresponding to the protonated form of the salt ([NH$_3$CH(CH$_3$)$_2$]$_2$O$_2$POCN+H$^+$), m/z 60 ([NH$_3$CH(CH$_3$)$_2$]$^+$), Negative ion, (FAB$^-$ DTT:DTE, 1:1) m/z 106 (NCP(O)—(OH)O$^-$). High resolution mass spectroscopy. Observed mass, 167.0592. Calculated mass for [C$_4$H$_{11}$PN$_2$O$_3$+H$^+$], 167.0585.

Example 8
Bis(trimethylsulfonium)Cyanophosphonate

This reaction was carried out with diethyl cyanophosphonate (0.2 g, 1.23 mmol) and trimethylsilyl iodide (0.55 g, 2.75 mmol). After removing the volatile components, isopropanol (1 mL) was added at 0° C., forming cyanophosphonic acid, which was not isolated. The isopropanol was evaporated and replaced with methanol (2 mL) and the solution was cooled to −35° C. To this solution, trimethyl sulfonium hydroxide (10 mL of a 0.25 M solution in CH$_3$OH, 2.5 mmol) was slowly added. The methanol was removed, giving an oil, which after drying under vacuum overnight, was cooled in the refrigerator at −4° C. for 3 days to form 0.15 g (0.58 mmol, 47% yield) of the extremely hygroscopic crystalline product. $^{31}$P NMR (CD$_3$OD) δ (ppm) −22.9 (s); Mass spectrum: (FAB$^+$ DTT:DTE, 1:1) m/z 260, corresponding to the protonated form of the salt [(S(CH$_3$)$_3$)$_2$O$_2$POCN+H$^+$], m/z 77, [S(CH$_3$)$_3$$^+$]; Anionic species (FAB$^-$ DTT:DTE, 1:1) m/z 106 [(NC)P(O)(OH)O$^-$]. High resolution mass spectroscopy: Observed mass, 260.0528. Calculated mass for [C$_7$H$_{18}$NO$_3$PS$_2$+H]$^+$, 260.0544.

Example 9
Bis(triethylammonium)Cyanophosphonate

Cyanophosphonic acid was prepared using isopropanol according to the procedure described in Example 3. The isopropanol was removed under reduced pressure and replaced by dry acetone (10 mL). To this solution triethylamine (4.23 g, 0.03 mol) in acetone (2 mL) was slowly added at −20° C. The acetone was removed, giving an oil, which after drying under vacuum overnight, was cooled in the refrigerator at −4° C. for 3 days to form 4.8 g (0.016 mol, 52% yield) of the hygroscopic crystalline product which according to $^{31}$P NMR contained up to 6.3% impurities. $^{31}$P NMR (CD$_3$OD) δ (ppm) −16.9 (major peak, 93.7%), minor signals: −6 to −6.6 (2.6%), 1.2 to 2.0 (3.7%); $^1$H NMR (D$_2$O) δ (ppm) 1.08 (t), 3.04 (q); $^{13}$C NMR (D$_2$O) δ (ppm)

8, 43, and 123.6 (d, $^1J_{CP}$=142.6 Hz). Mass spectrum (FAB$^+$, thioglycerol) m/z 310, corresponding to the protonated form of salt [(HN(C$_2$H$_5$)$_3$)$_2$O$_2$POCN+H$^+$], m/z 102 [(HN(C$_2$H$_5$)$_3$$^+$]; Negative ion (FAB$^-$, thioglycerol) at m/z 106 [NCP(O)(OH)O$^-$], and to the clusters [NCP(O)(OH)O]—H[NCP(O)(OH)O$^-$]$^-$ at m/z 213, and [NCP(O)(OH)O$^-$]H[NCP(O)(OH)O]H[NCP(O)—(OH)O$^-$]$^-$ at m/z 320).

Example 10
Bis(tetramethylammonium)Cyanophosphonate

Cyanophosphonic acid was prepared with isopropanol according to the procedure in Example 3 using the same molar quantities. The isopropanol was removed under reduced pressure and replaced with methanol (6 mL). To this solution tetramethylammonium hydroxide pentahydrate (4.53 g, 0.025 mol) in methanol (6 mL) was slowly added at –20° C. The methanol was removed, giving an oil, which after drying under vacuum overnight, was cooled in the refrigerator at –4° C. for 2 days to form 4.3 g (0.017 mol, 68% yield) of the hygroscopic crystalline product which according to $^{31}$P NMR contained up to 14.7% impurities. $^{31}$P NMR (D$_2$O) δ (ppm) –14.4 (major peak, 85.3%), minor signals: 0.70, 1.05, and 3.0; $^1$H NMR (D$_2$O) δ (ppm) 3.0 (s); $^{13}$C NMR (D$_2$O) δ (ppm) 55 (q, J=4.0 Hz), 123.7 (d, $^1J_{CP}$=142.6 Hz). Mass spectrum (FAB$^+$, thioglycerol) m/z 254, corresponding to the protonated form of salt [(N(CH$_3$)$_4$)$_2$O$_2$POCN+H$^+$], m/z 74 [(N(CH$_3$)$_4$$^+$]; Negative ion (FAB$^-$, thioglycerol) at m/z 106 [NCP(O)(OH)—O$^-$], and to the cluster [NCP(O)(OH)O$^-$]H[NCP(O)(OH)O$^-$]$^-$ at m/z 213.

Example 11
Bis(tetrabutylammonium)Cyanophosphonate

Cyanophosphonic acid was prepared using isopropanol according to the procedure described in Example 3. The isopropanol was removed under reduced pressure and replaced with methanol (6 mL). To this solution tetrabutyl ammonium hydroxide (25 mL of a 1.0 M solution in CH$_3$OH, 25 mmol) was slowly added at –20° C. The methanol was removed, giving a crude oil which according to $^{31}$P NMR contained up to 34% impurities. $^{31}$P NMR (D$_2$O) δ (ppm) –14.1 (major peak, 66.2%), minor signals: –20.9 (7.0%) and 2.2 to 2.7 (26.8%). After extraction into dichloromethane the spectral yield of product increased to 80%: $^{31}$P NMR (CD$_2$Cl$_2$) δ (ppm) –13.0 (major peak, 80.1%), minor signals: –20.5 (13.5%) and 3.0 (6.4%). $^{13}$C NMR (CD$_3$OD) δ (ppm) 11.5, 18.2 (t, J=1.5 Hz), 22.3 (s), 57.0 (t, J=2.7 Hz), and 122.8 (d, $^1J_{CP}$=144.3 Hz). Removal of the solvent gave 9.7 g of oil (0.016 mol., 66% yield). Mass spectrum (FAB$^+$, thioglycerol) m/z 102, corresponding to [N(C$_4$H$_9$)$_4$$^+$]; Negative ion (FAB$^-$, thioglycerol) at m/z 106 [NCP(O)(OH)O$^-$].

General Procedure for Examples 12 to 20

Equal molar parts of diethyl cyanophosphonate and ammonium, sulfonium or phosphonium halide salts (Cl, Br, I) were mixed in a minimal amount of dry polar solvent such as DMF, acetonitrile, dimethylacetamide, DMSO, acetone, etc. The magnetically stirred reaction mixture was heated to 70° to 80° C. for 1 to 2 hours, or was kept at room temperature overnight under inert atmosphere. The solvent was removed under reduced pressure, or the product was precipitated by addition of excess ether-acetone (10:1) to obtain an oil (for alkyl ammonium salts) or crystals for sulfonium and phosphonium salts.

Example 12
Isopropylammonium Ethyl Cyanophosphonate

Diethyl cyanophosphonate (0.50 g, 3.06 mmol) and isopropylammonium chloride (0.29 g, 3.03 mmol) were added to DMF (3 mL) and the reaction mixture was stirred overnight. The solvent was removed under reduced pressure to give 0.48 g (88% yield) of an oil which was analyzed by NMR and mass spectrometry without additional purification. $^{31}$P NMR (CD$_2$Cl$_2$) δ (ppm) –21.2 (t, $^3J_{PH}$=8.4 Hz); $^{13}$C NMR (CD$_2$Cl$_2$) δ (ppm) 121.0 (d, $^1J_{CP}$=177.8 Hz), 63.2 (d, $^2J_{CP}$6.3 Hz), 42.1 (s), 20.9 (s), 16.0 (d, $^3J_{CP}$=7.5 Hz). Mass spectral analysis (FAB$^+$ TGL) detected the peak at m/z 195, corresponding to the protonated form of the salt [$^+$NH$_3$CH(CH$_3$)$_2$—O(OC$_2$H$_5$)POCN+H$^+$], the presence of the cation at m/z 60 ([NH$_3$CH(CH$_3$)$_2$]$^+$) and an anionic species (FAB$^-$, TGL) at m/z 134 [NCP(O)(OC$_2$H$_5$)O$^-$].

Example 13
(Ethyl 2-Ammonium Acetate)Ethyl Cyanophosphonate

Diethyl cyanophosphonate (0.50 g, 3.06 mmol) and ethyl glycinate hydrochloride (0.425 g, 3.05 mmol) were added to DMF (3 mL) which was then heated to 80° C. for 1 hour. The solvent was removed under reduced pressure to give 0.63 g (86% yield) of a viscous residue which was analyzed by NMR and mass spectrometry without additional purification. $^{31}$P NMR (CD$_2$Cl$_2$) δ (ppm) –20.5 (t, $^3J_{PH}$=7.6 Hz); $^{13}$C NMR (CD$_2$Cl$_2$) δ (ppm) 168 (s), 121.0 (d, $^1J_{CP}$=178.9 Hz), 62.9 (d, $^1J_{CP}$=6.3 Hz), 62.5 (s), 41.6 (s), 16.0 (d, $^3J_{CP}$=7.4 Hz), 13.9 (s). Mass spectral analysis (FAB$^+$ DTT:DTE, 1:1) detected a peak at m/z 239, corresponding to the protonated form of the salt [$^+$NH$_3$CH$_2$C(O)OC$_2$H$_5$-O(OC$_2$H$_5$)POCN+H$^+$], the presence of a cation at m/z 104 ([NH$_3$CH$_2$C(O)OC$_2$H$_5$]$^+$) and an anionic species (FAB$^-$, DTT:DTE, 1:1) at m/z 134 [NCP(O)(OC 2H)O$^-$].

Example 14
Trimethylsulfonium Ethyl Cyanophosphonate

Diethyl cyanophosphonate (0.50 g, 3.06 mmol) and trimethylsulfonium iodide (0.624 g, 3.06 mmol) were added to dimethylacetamide (1 mL) which was heated to 80° C. for 3 hours. Then ether (9 mL) containing 1 mL of acetone was added, giving an oil which was crystallized within 15 minutes. This solid was dissolved in dry cold acetone (1 mL) and precipitated with ether (10 mL). The solid was filtered to give 0.48 g (74% yield) of product. $^{31}$P NMR (acetone-d$_6$) δ (ppm) –22.2 (t, $^3J_{PH}$=7.6 Hz); $^{13}$C NMR (acetone-d$_6$) δ (ppm) 122.0 (d, $^1J_{CP}$154.3 Hz), 61.8 (d, $^2J_{CP}$=6.3 Hz), 26.9 (s), 16.6 (d, $^3J_{CP}$=7.2 Hz). Mass spectral analysis (FAB$^+$, DTT:DTE, 1:1) detected a peak at m/z 288, corresponding to the complex [[$^+$S(CH$_3$)$_3$$^-$O(OC$_2$H$_5$)POCN] [S(CH$_3$)$_3$]$^+$], the presence of a cation at m/z 77 ([S(CH$_3$)$_3$]$^+$) and an anionic species (FAB$^-$, DTT:DTE, 1:1) at m/z 134 [NCP(O)(OC$_2$H$_5$)O$^-$]. Elemental analysis: Found: C, 33.89%; H, 6.42%; N, 6.48%; I, 0.0%; Calculated for C$_6$H$_{14}$NO$_3$PS: C, 34.12%; H, 6.68%; N, 6.63%.

Example 15
Tetramethylphosphonium Ethyl Cyanophosphonate

Diethyl cyanophosphonate (0.50 g, 3.06 mmol) and tetramethylphosphonium bromide (0.523 g, 3.06 mmol) were added to dimethylacetamide (0.5 mL) which was heated to 80° C. for 3 hours. Then dimethylacetamide was removed under vacuum to give solid residue and 10 mL of ether was added to it, yielding 0.39 g (57% yield) of product. $^{31}$P NMR (CD$_2$Cl$_2$) δ (ppm) –33.9 (m, $^2J_{PH}$=15.0 Hz), –19.8 ; $^{13}$C NMR (CD$_2$Cl$_2$) δ (ppm) 121.3 (d, $^1J_{CP}$=152.9 Hz), 61.2 (d, $^2J_{CP}$=6.6 Hz), 15.8 (d, $^3J_{CP}$=7.5 Hz), 9.1 (d, $^2J_{CP}$=55.8 Hz). Mass spectral analysis (FAB$^+$, TGL) detected a peak at m/z 316.1, corresponding to the complex species [[$^+$P(CH$_3$)$_4$$^-$O(OC$_2$H$_5$)POCN][P(CH$_3$)$_4$]$^+$], the presence of a cation at m/z 90.9 [[P(CH$_3$)$_4$]$^+$] and an anionic species (FAB$^-$ TGL) at m/z 133.9 [NCP(O)(OC$_2$H$_5$)O $^-$]. Elemental analysis:

Found, C, 37.14%; H, 7.26%; N, 6.16%; I, 0.0%; Calculated for [(C$_2$H$_5$O)OP(CH$_3$)$_4$]$^+$ [OPOCN]$^-$, C, 37.34%; H, 7.61%; N, 6.22%.

Example 16
Sodium Ethyl Cyanophosphonate

Diethyl cyanophosphonate (4.0 g, 24.5 mmol) and NaI (3.68 g, 24.5 mmol) were added to dry acetonitrile (10 mL) which was magnetically stirred at room temperature for 20 minutes giving a white solid which was filtered and washed with ether (15 mL) yielding 3.0 g (78% yield) of [Na$^+$ (C$_2$H$_5$O)($^-$O)POCN]. $^{31}$P NMR (D$_2$O) δ (ppm) −19.8 (t, $^3J_{PH}$=9.2 Hz); $^{13}$C NMR (D$_2$O) δ (ppm) 117.9 (d, $^1J_{CP}$= 189.3 Hz), 63.5 (d, $^2J_{CP}$=6.3 Hz), 15.1 (d, $^3J_{CP}$=6.9 Hz). Mass spectral analysis (FAB$^+$ TGL) detected a peak at m/z 316.1, corresponding to the complex species [[Na$^{+-}$O (OC$_2$H$_5$)POCN][Na]$^+$], an anionic species (FAB$^-$, TGL) at m/z 133.9 [NCP(O)(OC$_2$H$_5$)O $^-$], and to the cluster [Na$^+$O (OC$_2$H$_5$)POCN$^-$]O(OC$_2$H$_5$)POCN]$^-$ at m/z 290.9.

Example 17
Triethylammonium Ethyl Cyanophosphonate

Diethyl cyanophosphonate (0.50 g, 3.06 mmol) and triethylamine hydrochloride (0.421 g, 3.06 mmol) were added to dimethylacetamide (0.5 mL) which was heated to 80° C. for 3 hours. Then dimethylacetamide was removed under vacuum to give 0.42 g (67% yield) of a viscous residue which was analyzed by NMR and mass spectrometry without additional purification. $^{31}$P NMR (D$_2$O) δ (ppm) major peak (94.7%) −19.6 (t, $^3J_{PH}$=9.3 Hz), minor peak (5.3%) −12.1; $^1$H NMR (D$_2$O) δ (ppm) 1.25 (tr), 3.20 (q), and 4.05 (qnt); $^{13}$C NMR (D$_2$O) δ (ppm) 119.9 (d, $^1J_{CP}$=174.35 Hz), 63.9 (d, $^2J_{CP}$=6.6 Hz), 47.0 (t, J=4.0 Hz) 16.0 (d, $^3J_{CP}$=6.8 Hz), 9.1 (s). Mass spectral analysis (FAB$^+$, thioglycerol) detected a peak at m/z 338.4, corresponding to the complex species [[$^+$HN(C$_2$H$_5$ )$_3$]$_2$—O(OC$_2$H$_5$)POCN]$^+$], the presence of a cation at m/z 102 [[HN(C$_2$H$_5$)$_3$]$^+$] and an anionic species (FAB$^-$ thioglycerol) at m/z 133.9 [NCP(O)(OC$_2$H$_5$)O $^-$], its protonated dimer at m/z 268.9 [(H+) O(OC$_2$H$_5$)POCN$^-$][O(OC$_2$H$_5$)POCN]$^-$, and to the cluster [[$^+$HN(C$_2$H$_5$)$_3$]O(OC$_2$H$_5$)POCN$^-$][O(OC$_2$H$_5$)POCN]$^-$ at m/z 370.1.

Example 18
Tetramethylammonium Ethyl Cyanophosphonate

Diethyl cyanophosphonate (0.50 g, 3.06 mmol) and tetramethylammonium chloride (0.338 g, 3.06 mmol) were added to dimethylacetamide (0.5 mL) which was heated to 80° C. for 3 hours. Then dimethylacetamide was removed under vacuum to give 0.45 g (70% yield) of a viscous residue which was analyzed by NMR and mass spectrometry without additional purification. $^{31}$P NMR (CD$_3$CN) δ (ppm) major peak (87%) −22.4 (t, $^3J_{PH}$=8.8 Hz), minor peaks: −13.0 to −14.0 (10%), −3.0 (3%); $^1$H NMR (D$_2$O) δ (ppm) 1.30 (t), 3.20 (s), and 4.05 (qnt); $^{13}$C NMR (D$_2$O) δ (ppm) 119.7 (d, $^1J_{CP}$= 175.5 Hz), 63.9 (d, $^2J_{CP}$=6.3 Hz), 55.8 (t, J=4.0 Hz) 16.0 (d, $^3J_{CP}$=6.87 Hz). Mass spectral analysis (FAB$^+$, thioglycerol) detected a peak at m/z 282.3, corresponding to the complex species [[$^+$N(CH$_3$)$_4$]$_2$$^-$O(OC$_2$H$_5$) POCN]$^+$], the presence of a cation at m/z 74.1 [[N(CH$_3$)$_4$]$^+$] and an anionic species (FAB$^-$ thioglycerol) at m/z 133.9 [NCP(O)(OC$_2$H$_5$)O$^-$], and to the cluster [[$^+$N(CH$_3$)$_4$] O(OC$_2$H$_5$)POCN$^-$[O(OC$_2$H$_5$)POCN]$^-$ at m/z 342.

Example 19
Tetrabutylammonium Ethyl Cyanophosphonate

Diethyl cyanophosphonate (0.50 g, 3.06 mmol) and tetrabutylammonium bromide (0.990 g, 3.06 mmol) were added to methylene chloride (2 mL) which was heated to 40° C. for 3 hours. Then methylene chloride was removed under vacuum to give 1.03 g (89% yield) of a white solid product which was analyzed by NMR and mass spectrometry without additional purification. $^{31}$P NMR (CD$_2$Cl$_2$) δ (ppm) −19.6 (t, $^3J_{PH}$=8.4 Hz), (D$_2$O) −20.1 (t, $^3J_{PH}$=9.15 Hz) $^1$H NMR (D$_2$O) δ (ppm) 0.85 (t), 1.30 (sxt), 1.55 (qnt), 3.10 (t), and 4.05 (qnt); $^{13}$C NMR (D$_2$O) δ (ppm) 118.5 (d, $^1J_{CP}$= 177.2 Hz), 63.1 (d, $^2J_{CP}$=6.6 Hz), 57.8, 23.0, 18.4, 15.0 (d, $^3J_{CP}$=6.58 Hz). Mass spectral analysis (FAB$^+$, thioglycerol) detected a peak at m/z 242.3, corresponding to the cation at m/z 242.3 [[N(C$_4$H$_9$)$_4$]$^+$] and an anionic species (FAB$^-$ thioglycerol) at m/z 133.9 [NCP(O)(OC$_2$H$_5$)O $^-$], its protonated dimer at m/z 268.9 [(H+) O(OC$_2$H$_5$)POCN$^-$][O (OC$_2$H$_5$)POCN]$^-$, and to the cluster [[N(C$_4$H$_9$)$_4$]$^+$] O(OC$_2$H$_5$)POCN$^-$[O(OC$_2$H$_5$)—POCN]$^-$ at m/z 510.6.

Example 20
Trimethylsulfoxonium Ethyl Cyanophosphonate

Diethyl cyanophosphonate (0.50 g, 3.06 mmol) and trimethylsulfoxonium iodide (0.673 g, 3.06 mmol) were added to dimethylacetamide (1 mL) which was heated to 80° C. for 1 hour. Then ether (9 mL) containing 1 mL of acetone was added to give 0.47 g (78% yield) of a viscous residue which was crystallized within 15 hours. It was washed by CH$_2$Cl$_2$ and dried under vacuum, and analyzed by NMR and mass spectrometry. $^{31}$P NMR (D$_2$O) δ (ppm) −19.7 (t, $^3J_{PH}$=9.15 Hz); $^1$H NMR (D$_2$O) δ (ppm) 1.22 (t), 3.78 (s), and 4.05 (qnt); $^{13}$C NMR (D$_2$O) δ (ppm) 118.1 (d, $^1J_{CP}$=178.9 Hz), 63.3 (d, $^1J_{CP}$=6.3 Hz), 39.5, 15.0 (d, $^3J_{CP}$=6.87 Hz). Mass spectral analysis (FAB$^+$, DTT:DTE, 1:1) detected a peak at m/z 320.1, corresponding to the complex [[$^+$OS(CH$_3$)$_3$$^-$O (OC$_2$H$_5$)POCN] [OS(CH$_3$)$_3$]$^+$], the presence of a cation at m/z 93 ([OS(CH$_3$)$_3$]$^+$) and an anionic species (FAB$^-$, DTT:DTE, 1:1) at m/z 134 [NCP(O)(OC$_2$H$_5$)O $^-$].

Example 21
General Procedure for Low Pressure Hydrogenations

Dipotassium cyanophosphonate (0.133 g, 1.0 mmol) was added to Raney nickel (0.118 g, as a 50% slurry in water, W2 form) in a Fisher Porter bottle containing a stir bar. Water (5 mL) was added, and platinum tetrachloride (0.105 g, 0.31 mmol) was added. The pressure bottle was immediately connected to a hydrogen manifold, and three purges with hydrogen at 75 psi were done, and the bottle was pressurized to 75 psi. The reaction mixture was vigorously stirred for 25.5 hours at room temperature. The pressure was then released and the reaction mixture was filtered. A 63% yield of aminomethylphosphonic acid was determined by HPLC analysis.

Example 22
General Procedure for Hydrogenation in Autoclave

To a 300 mL Autoclave Engineers autoclave, Na$_2$O$_3$PCN (H$_2$O)$_{0.49}$ (0.80 g, 5.0 mmol) was added, followed by 10% Pt/C (0.15 g), water (100 mL), and then HCl-dioxane (2.5 mL, 4 N, 10.0 mL). The autoclave was sealed, pressured once with nitrogen above 500 psi, vented, and pressured with hydrogen to 1001 psi. Stirring at about 1500 rpm was started. Within about 10 minutes, the internal pressure was about 996 psi, and the autoclave internal temperature was about 26° C. After stirring overnight, the hydrogen was vented, the autoclave was repressurized with nitrogen and vented, and then the reactor was opened and the reaction mixture removed. The reaction mixture was filtered, and the resulting solution analyzed by HPLC. The yield of aminomethylphosphonic acid determined by HPLC was 85%, and 87% by NMR.

All of the compositions and methods disclosed and claimed herein can be made and executed without undue experimentation in light of the present disclosure. While the compositions and methods of this invention have been described in terms of preferred embodiments, it will be apparent to those of skill in the art that variations can be applied to the process described herein without departing from the concept, spirit and scope of the invention. All such similar substitutes and modifications apparent to those skilled in the art are deemed to be within the spirit, scope and concept of the invention.

What is claimed is:

1. A cyanophosphonate salt of the formula (I):

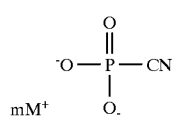

(I)

wherein M⁺ is one or more suitable monovalent or polyvalent cations and m is the number of M⁺ cations, wherein M⁺ comprises an alkali metal cation, an alkaline earth metal cation, a transition metal cation, a group III metal cation, a lanthanide, an actinide, a cationic form of a primary amine, a cationic form of a secondary amine of molecular weight less than 175 g/mol, a cationic form of a secondary amine of molecular weight greater than 185 g/mol, a cationic form of a tertiary amine, a cationic form of a polyamine, a cationic form of an amino acid, a cationic form of a dendrimeric amine, a cationic form of a heterocycle, ammonium, a quarternary ammonium, a cationic hydrazine derivative, an amidinium, a sulfoxonium, a sulfonium, a phosphonium, a guanidinium, a cationic form of a biologically active amine or mixtures thereof.

2. The compound of claim 1, wherein M⁺ is an alkali metal cation.

3. The compound of claim 2, wherein M⁺ is a lithium cation, a sodium cation or a potassium cation.

4. The compound of claim 1, wherein M⁺ is an ammonium cation.

5. The compound of claim 4, wherein M⁺ is an ammonium derivative.

6. The compound of claim 5, wherein M⁺ is an isopropylammonium cation.

7. The compound of claim 5, wherein M⁺ is a dimethylammonium cation.

8. The compound of claim 5, wherein M⁺ is a 2-hydroxyethylammonium cation.

9. The compound of claim 5, wherein M⁺ is a triethylammonium cation.

10. The compound of claim 5, wherein M⁺ is a trimethylammonium cation.

11. The compound of claim 5, wherein M⁺ is a tetramethylammonium cation.

12. The compound of claim 5, wherein M⁺ is a tetrabutylammonium cation.

13. The compound of claim 1, wherein M⁺ is a sulfonium cation.

14. The compound of claim 13, wherein M⁺ is a trimethylsulfonium cation.

15. The compound of claim 1, wherein M⁺ is a phosphonium cation.

16. The compound of claim 15, wherein M⁺ is a tetramethylphosphonium cation.

17. The compound of claim 1, wherein M⁺ is a sulfoxonium cation.

18. The compound of claim 17, wherein M⁺ is a trimethylsulfoxonium cation.

19. The compound of claim 1, wherein mM⁺ represents two potassium cations, two sodium cations, two lithium cations, two 2-hydroxyethylammonium cations, two ammonium cations, two dimethylammonium cations, two isopropylammonium cations, two trimethylsulfonium cations, two triethylammonium cations, two tetramethyl ammonium cations or two tetrabutylammonium cations.

20. The compound of claim 1, wherein mM⁺ represents a potassium cation and a sodium cation, a lithium cation and a sodium cation, a potassium cation and a lithium cation, an ammonium cation and a sodium cation, an ammonium cation and a potassium cation, an ammonium cation and a sulfonium cation, a sulfonium cation and an alkylammonium cation, an ammonium cation and an alkylammonium cation, a sodium cation and a sulfonium cation, a potassium cation and a sulfonium cation, a sodium cation and an alkylammonium cation or a potassium cation and an alkylammonium cation.

21. The compound of claim 1, wherein the cation is herbicidally active.

22. A cyanophosphonate monoacid salt of formula (II):

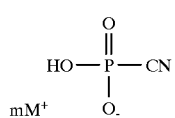

(II)

wherein M⁺ is one or more suitable monovalent or polyvalent cations and m is the number of M⁺ cations.

23. The compound of claim 22, wherein M⁺ comprises an alkali metal cation, an alkaline earth metal cation, a transition metal cation, a group III metal cation, a lanthanide, an actinide, a cationic form of a primary amine, a cationic form of a secondary amine, a cationic form of a tertiary amine, a cationic form of a polyamine, a cationic form of an amino acid, a cationic form of a dendrimeric amine, a cationic form of a heterocycle, ammonium, a quarternary ammonium, a cationic hydrazine derivative, an amidinium, a sulfoxonium, a sulfonium, a phosphonium, a guanidinium, a cationic form of a biologically active amine or mixtures thereof.

24. The compound of claim 23, wherein M⁺ is an alkali metal cation.

25. The compound of claim 24, wherein M⁺ is a lithium cation, a sodium cation or a potassium cation.

26. The compound of claim 23, wherein M⁺ is an ammonium cation.

27. The compound of claim 26, wherein M⁺ is an ammonium derivative.

28. The compound of claim 27, wherein M⁺ is an isopropylammonium cation.

29. The compound of claim 27, wherein M⁺ is a dimethylammonium cation.

30. The compound of claim 27, wherein M⁺ is a 2-hydroxyethylammonium cation.

31. The compound of claim 27, wherein M⁺ is a triethylammonium cation.

32. The compound of claim 27, wherein M⁺ is a trimethylammonium cation.

33. The compound of claim 27, wherein M⁺ is a tetramethylammonium cation.

34. The compound of claim 27, wherein M⁺ is a tetrabutylammonium cation.

35. The compound of claim 23, wherein M⁺ is a sulfonium cation.

36. The compound of claim 35, wherein M⁺ is a trimethylsulfonium cation.

37. The compound of claim 23, where M⁺ is a phosphonium cation.

38. The compound of claim 37, wherein M⁺ is a tetramethylphosphonium cation.

39. The compound of claim 23, wherein M⁺ is a sulfoxonium cation.

40. The compound of claim 39, wherein M⁺ is a trimethylsulfoxonium cation.

41. The compound of claim 22, wherein the cation is herbicidally active.

42. A cyanophosphonate derivative of the formula (III):

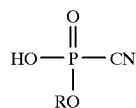

wherein R is:
an alkyl group containing 2–20 carbons;
an aryl group; or
an arylalkyl group.

43. The compound of claim 42, wherein the alkyl group is ethyl or propyl.

44. The compound of claim 42, wherein the aryl group is phenyl.

45. The compound of claim 42, wherein the arylalkyl group is benzyl or 62 -phenylethyl.

46. A cyanophosphonate monoester salt of the formula (IV):

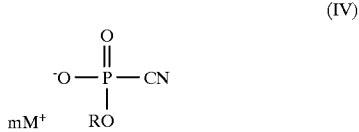

wherein M⁺ is one or more suitable monovalent or polyvalent cations, m is the number of M⁺ cations and R is an alkyl, aryl, arylalkyl or functionalized group containing 2 to 20 carbons.

47. The compound of claim 46, wherein the alkyl group is ethyl or propyl.

48. The compound of claim 46, wherein the aryl group is phenyl.

49. The compound of claim 46, wherein the arylalkyl group is benzyl.

50. The compound of claim 46, wherein M⁺ comprises an alkali metal cation, an alkaline earth metal cation, a transition metal cation, a group III metal cation, a lanthanide, an actinide, a cationic form of a primary amine, a cationic form of a secondary amine, a cationic form of a tertiary amine, a cationic form of a polyamine, a cationic form of an amino acid, a cationic form of a dendrimeric amine, a cationic form of a heterocycle, ammonium, a quarternary ammonium, a cationic hydrazine derivative, an amidinium, a sulfoxonium, a sulfonium, a phosphonium, a guanidinium, a cationic form of a biologically active amine or mixtures thereof.

51. The compound of claim 50, wherein M⁺ is an alkali metal cation.

52. The compound of claim 51, wherein M⁺ is a lithium cation, a sodium cation or a potassium cation.

53. The compound of claim 50, wherein M⁺ is an ammonium cation.

54. The compound of claim 53, wherein M⁺ is an ammonium derivative.

55. The compound of claim 54, wherein M⁺ is an isopropylammonium cation.

56. The compound of claim 54, wherein M⁺ is a dimethylammonium cation.

57. The compound of claim 54, wherein M⁺ is a 2-hydroxyethylammonium cation.

58. The compound of claim 54, wherein M⁺ is a triethylammonium cation.

59. The compound of claim 54, wherein M⁺ is a trimethylammonium cation.

60. The compound of claim 54, wherein M⁺ is a tetramethylammonium cation.

61. The compound of claim 54, wherein M⁺ is a tetrabutylammonium cation.

62. The compound of claim 50, wherein M⁺ is a sulfonium cation.

63. The compound of claim 62, wherein M⁺ is a trimethylsulfonium cation.

64. The compound of claim 50, wherein M⁺ is a phosphonium cation.

65. The compound of claim 64, wherein M⁺ is a tetramethylphosphonium cation.

66. The compound of claim 50, wherein M⁺ is a sulfoxonium cation.

67. The compound of claim 66, wherein M⁺ is a trimethylsulfoxonium cation.

68. The compound of claim 46, wherein the cation is herbicidally active.

69. The compound of claim 46, wherein formula (IV) is isopropylammonium ethyl cyanophosphonate, (ethyl 2-ammonium acetate)ethyl cyanophosphonate, trimethylsulfonium ethyl cyanophosphonate, tetramethylphosphonium ethyl cyanophosphonate, sodium ethyl cyanophosphonate, triethylammonium ethyl cyanophosphonate, tetramethylammonium ethyl cyanophosphonate, tetrabutylammonium ethyl cyanophosphonate or trimethylsulfoxonium ethyl cyanophosphonate.

70. A cyanophosphonate methylester of the formula (V):

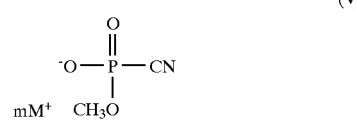

wherein M⁺ is one or more suitable monovalent or polyvalent cations and m is the number of M⁺ cations, wherein M⁺ comprises a potassium cation, a lithium cation, an alkaline earth metal cation, a transition metal cation, a group III metal cation, a lanthanide, an actinide, a cationic form of a primary amine, a cationic form of a secondary amine, a cationic form of a tertiary amine, a cationic form of a polyamine, a cationic form of an amino acid, a cationic form of a dendrimeric amine, a cationic form of a heterocycle, ammonium, a quarternary ammonium, a cationic hydrazine derivative, an amidinium, a sulfoxonium, a sulfonium, a phosphonium, a guanidinium or a cationic form of a biologically active amine.

71. The compound of claim 70, wherein M⁺ is a lithium cation or a potassium cation.

72. The compound of claim 70, wherein M⁺ is an ammonium cation.

73. The compound of claim 72, wherein M⁺ is an ammonium derivative.

74. The compound of claim 73, wherein M⁺ is an isopropylammonium cation.

75. The compound of claim 73, wherein M⁺ is a dimethylammonium cation.

76. The compound of claim 73, wherein M⁺ is a 2-hydroxyethylammonium cation.

77. The compound of claim 73, wherein M⁺ is a triethylammonium cation.

78. The compound of claim 73, wherein M⁺ is a trimethylammonium cation.

79. The compound of claim 73, wherein M⁺ is a tetramethylammonium cation.

80. The compound of claim 73, wherein M⁺ is a tetrabutylammonium cation.

81. The compound of claim 70, wherein M⁺ is a sulfonium cation.

82. The compound of claim 81, wherein M⁺ is a trimethylsulfonium cation.

83. The compound of claim 70, wherein M⁺ is a phosphonium cation.

84. The compound of claim 83, wherein M⁺ is a tetramethylphosphonium cation.

85. The compound of claim 70, wherein M⁺ is a sulfoxonium cation.

86. The compound of claim 85, wherein M⁺ is a tetramethylsulfoxonium cation.

87. The compound of claim 70, wherein the cation is herbicidally active.

88. A cyanophosphonate derivative of the formula:

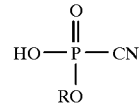

wherein R is selected from the group consisting of 2-aminoethyl, choline, 2-hydroxyethyl, glycerol, propylene glycol, serine, threonine, tyrosine, glucose, sucrose, fructose, galactose, mannose, pentaerythritol, tetra(hydroxymethyl)methane, and tetrakis(hydroxymethyl)phosphonium.

* * * * *

UNITED STATES PATENT AND TRADEMARK OFFICE
CERTIFICATE OF CORRECTION

PATENT NO. : 5,935,542

DATED : August 10, 1999

INVENTOR(S) : Patrick J. Lennon and Sergey G. Vulfson

It is certified that error appears in the above-identified patent and that said Letters Patent is hereby corrected as shown below:

Claim 45, line 30, please delete "62" and insert there of --β--.

Signed and Sealed this

Nineteenth Day of September, 2000

*Attest:*

Q. TODD DICKINSON

*Attesting Officer*        *Director of Patents and Trademarks*